United States Patent

Ikeda et al.

[11] Patent Number: 5,952,557
[45] Date of Patent: Sep. 14, 1999

[54] APPARATUS FOR ANALYZING A SILICON COMPOUND GAS FOR SILOXANE CONTENT

[75] Inventors: Takuya Ikeda; Toyohiko Abe, both of Tokyo, Japan

[73] Assignee: Nippon Sanso Corporation, Tokyo, Japan

[21] Appl. No.: 09/115,541

[22] Filed: Jul. 15, 1998

Related U.S. Application Data

[62] Division of application No. 09/015,780, Jan. 29, 1998.

[30] Foreign Application Priority Data

Feb. 20, 1997 [JP] Japan .................................. 9-036724
Feb. 28, 1997 [JP] Japan .................................. 9-046594

[51] Int. Cl.$^6$ ............................ G01N 30/04; G01N 7/00; G01N 31/12; E03B 31/00
[52] U.S. Cl. .................... 73/23.42; 73/23.2; 137/625.46; 422/80
[58] Field of Search ................................. 73/24.01, 23.2, 73/23.42, 864.21, 864.83; 137/625.11, 625.46; 422/80

[56] References Cited

U.S. PATENT DOCUMENTS

| | | | |
|---|---|---|---|
| 3,955,924 | 5/1976 | Northmore et al. .................... | 436/146 |
| 3,960,520 | 6/1976 | Allen ........................................... | 95/88 |
| 4,604,363 | 8/1986 | Newhouse et al. ...................... | 436/177 |
| 5,055,260 | 10/1991 | Roberge et al. ........................... | 422/62 |
| 5,289,715 | 3/1994 | Staples et al. .......................... | 73/24.01 |
| 5,312,947 | 5/1994 | Tsukuno et al. .......................... | 556/456 |

*Primary Examiner*—Hezron Williams
*Assistant Examiner*—Jay L. Politzer
*Attorney, Agent, or Firm*—Oblon, Spivak, McClelland, Maier & Neustadt, P.C.

[57] ABSTRACT

The present invention enables siloxanes which have a detrimental effect on the quality of products during semiconductor production to be efficiently removed from silicon compound gases, and enables minute amounts of siloxanes in these gases to be accurately measured to a few ppb, thus allowing for improvements in quality control by offering silicon compound gases of high purity. Diatomaceous earth M filled into a removal column 2 is heated by heating means provided on the removal column 2, while an inert gas such as nitrogen or helium is fed from an inert gas delivery pipe 13 via a pressure regulator 5 and an entry valve 6 into the removal column 2, and is allowed to flow out through an outlet valve 8 in order to thermally activate the diatomaceous earth M. After activation, the removal column is cooled to a temperature of 60-0° C., at which temperature a silicon compound gas S such as silane is fed through the pressure regulator 5 and the entry valve 6 into the removal column 2 so as to come into contact with the activated diatomaceous earth M. As a result, high-purity silicon compound gas which has been purified by removing siloxanes is let out through a gas vent pipe 9, from which it can be delivered through the outlet valve 8 to an area of use.

2 Claims, 12 Drawing Sheets

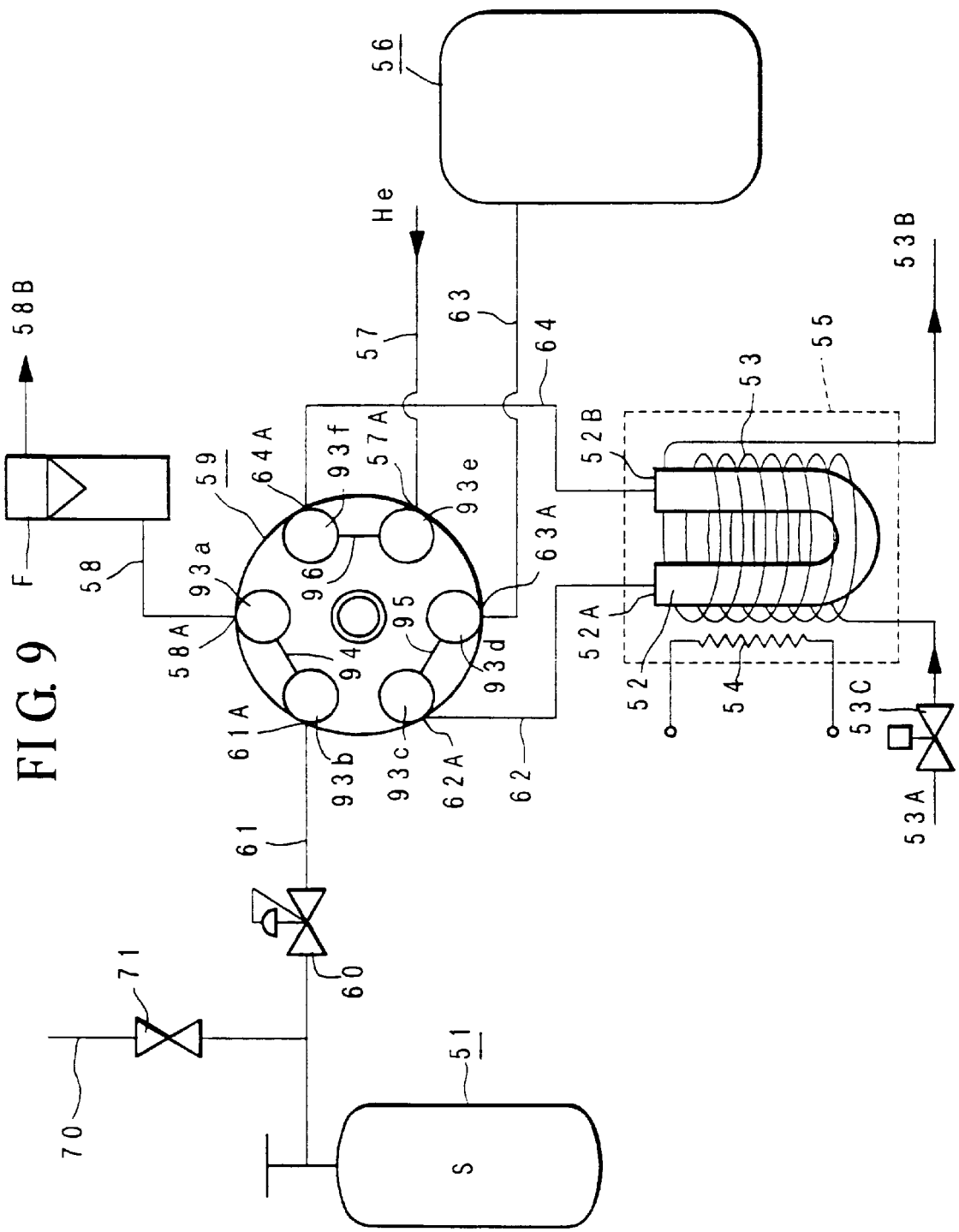

APPARATUS FOR ANALYZING A SILICON COMPOUND GAS FOR SILOXANE CONTENT

This application is a Division of application Ser. No. 09/015,780, filed on Jan. 29, 1998, pending.

BACKGROUND OF THE INVENTION

1. Field of the Invention

The present invention relates to a method and apparatus for removing siloxanes which have a detrimental effect on the quality of products and are contained in silicon compound gases such as monosilane, disilane, halides thereof, silicon tetrafluoride, silicon tetrachloride and the like which are useful as semiconductor material gases; and also relates to an analyzing method and analyzing apparatus for analyzing semiconductor material gases such as monosilane, disilane, halides thereof, silicon tetrafluoride, silicon tetrachloride and the like for the concentrations of siloxanes mixed therein, which can be effectively used to evaluate the quality of the gases.

This application is based on Patent Applications Nos. Hei 9-36724 and Hei 9-46594 filed in Japan, the contents of which are incorporated herein by reference.

2. Background Art

Silicon compound gases such as monosilane, disilane, halides thereof, silicon tetrafluoride, silicon tetrachloride and the like have been widely used in the semiconductor industry as materials for epitaxial growth or growth of silicon oxide films and nitride films. However, the presence of impurities contained in the above-mentioned silicon compound gases can have a considerable influence on the quality of the produced semiconductors. Specifically, the presence of oxygen-containing impurities such as water ($H_2O$) or carbon dioxide ($CO_2$) and the like can cause crystal defects which can lower the performance to the point of inadequacy. In particular, monosilane is known to have a tendency to react with water to produce detrimental siloxanes ($H_3Si$—O—$H_3Si$). For this reason, measures for preventing the intermixture of water have been taken.

Additionally, the siloxanes which have been produced and intermixed must be removed by purification in order to reduce the concentration to extremely low levels when using the above-mentioned silicon compound gases, and various methods have been proposed therefor. For example, an adsorption removal method using active alumina has been disclosed in Japanese Patent Application, Second Publication No. Sho 63-19443, an adsorption removal method using silica gel has been disclosed in Japanese Patent Application, Second Publication No. Hei 4-81523, and a removal method using getter metals has been disclosed in Japanese Patent Application, First Publication No. Hei 5-170405.

However, the above-mentioned conventional siloxane removal methods require the use of special agents such as getter metals, or the agents are difficult to activate favorably, so that they can contact monosilanes and cause the monosilanes to decompose and form hydrogen or disilanes. Additionally, since the adsorbents must be cooled to extremely low temperatures of below the ice point (0° C.) in order to increase the removal effect, the costs can rise so as to inflate expenditures and the operations are difficult to handle. Furthermore, even with the proposed removal methods given above, the removal of siloxanes from silicon compound gases such as monosilane, disilane, halides thereof, silicon tetrafluoride, silicon tetrachloride and the like has not attained the levels (content: a few ppb or less) which are held to be desirable in the semiconductor industry.

Additionally, the silicon compound gases such as monosilane, disilane, halides thereof, silicon tetrafluoride, silicon tetrachloride and the like without the siloxanes which are not desirable for retaining the quality of products are put to effective use as material gases for epitaxial growth or growth of silicon oxide and nitride films in the production of semiconductors. However, even after removal of siloxanes, trace amounts of siloxanes which have a detrimental effect of the quality of semiconductors remain mixed into the silicon compound gases. Therefore, due to increases in the scale of integration of semiconductors, the elimination of this siloxane content and the development of silicon compound gases of higher purity has been desired. In correlation therewith, the development of analysis techniques having lower minimum limits of sensitivity (a few ppb or less) for detecting siloxanes in silicon compound gases has become an essential prerequisite. That is, the development of high-quality material gases for the production of semiconductors containing extremely minute amounts of siloxanes is possible only after the establishment of an analysis method having a lower minimum limit for detection of siloxanes of only a few ppb or less as a method for analyzing gases to evaluate their quality.

Conventionally, silicon compound gases have been analyzed for siloxane content by using thermal-conductivity-detecting gas chromatography (hereinafter referred to as "TCD-GC") as a detection means. With this method, samples are analyzed by separating the components using as a separation column a stainless steel tube which is filled with Porapack P or Porapack Q (both products of Waters Corp.) composed of porous macromolecular agents such as divinylbenzene (DVB). According to this method, the detection sensitivity for siloxanes is merely 0.5–1 ppm (500–1000 ppb), which leaves impossible the detection of a few ppb which is required as described above.

Since the conventional TCD-GC analysis methods require the separation column to be heated to a temperature of 70–80° C. in order to conduct an analysis for siloxanes, the present inventors pinpointed the heating temperature as the likely cause of the minimum detection limits, and therefore measured the changes in the siloxane content by guiding gas discharged from the separation column to a mass spectrometer while changing the column temperature. The results are shown in FIG. 13. The separator which was used was Porapack P, the gas which was used was monosilane, of which 5 cc were collected for analysis at each temperature.

As is clear from FIG. 13, the amount of siloxanes from the column changes according to the temperature of the separation column, even if the same gas is analyzed. That is, when the temperature is high, the amount increases, so that the content of siloxanes was confirmed to be approximately 700–1200 ppb when the separation column had a temperature of 70–80° C. at which the gases are analyzed in TCD-GC, and was confirmed to achieve approximately 7000 ppb at a temperature of 100° C. On the other hand, at the lower temperatures, the content was lower, e.g. the content at 60° C. was approximately 300 ppb, and the content at 40° C. was approximately 60 ppb. This phenomenon is believed to be caused by reactions between trace amounts of residual water adhered to the macromolecular separator in the separation column and the silicon compounds which are introduced, which results in the production of siloxanes, of which the rate of production increases as the temperature rises.

Additionally, when analyzing silicon compound gases for siloxanes according to a conventional TCD-GC technique using heated separation columns, the amount of siloxanes extracted from the column changes depending on the temperature of the separation column, so that it is difficult to determine the true value. Furthermore, when the separation column used in this analysis method has a heating temperature of 70–80° C., the content of siloxanes is 700 ppb or more, which makes it impossible to detect the siloxane content in silicon compound gases in minute amounts of a few ppb, which is expected to become an essential requisite in this field.

SUMMARY OF THE INVENTION

The present invention has been made in consideration of the above-described circumstances, offers a method for efficiently and by simple operation removing and purifying siloxanes from silicon compound gases to desired minute amounts, and a removal apparatus therefor; and a high-sensitivity analyzing method and apparatus capable of measuring the siloxane content of silicon compound gases to minute amounts of a few ppb; and has the object of improving the quality of gases used in semiconductor production techniques which are becoming more highly integrated, and ensuring higher precision for analysis techniques such as to enable the evaluations of the quality of such high-quality gases.

In order to achieve the above purpose, a method for removing siloxanes from a silicon compound gas according to the present invention comprises steps of thermally activating diatomaceous earth by heating the diatomaceous earth; cooling the diatomaceous earth by feeding inert gas; and bringing the silicon compound gas into contact with the diatomaceous earth.

In this method, the heating temperature for activation of the diatomaceous earth should preferably be at least 150° C. Additionally, the cooling temperature after activation should preferably be 60-0° C.

Another method for removing siloxanes from a silicon compound gas according to the present invention comprises steps of thermally activating diatomaceous earth by feeding heated inert gas into contact with the diatomaceous earth; cooling the diatomaceous earth by feeding inert gas; and bringing the silicon compound gas into contact with the diatomaceous earth.

In this method, the heating temperature for activation of the diatomaceous earth should preferably be at least 150° C. Additionally, the cooling temperature after activation should preferably be 60-0° C.

Another method for removing siloxanes from a silicon compound gas according to the present invention comprises steps of thermally activating diatomaceous earth by directly heating the diatomaceous earth and by feeding heated inert gas into contact with the diatomaceous earth; cooling the diatomaceous earth by feeding inert gas; and bringing the silicon compound gas into contact with the diatomaceous earth.

In this method, the heating temperature for activation of the diatomaceous earth should preferably be at least 150° C. Additionally, the cooling temperature after activation should preferably be 60-0° C.

An apparatus for removing siloxanes from a silicon compound gas according to the present invention comprises a removal column filled with diatomaceous earth; a pressure regulator provided in communication with a silicon compound gas source by way of a supply pipe; a gas feed pipe provided in communication with the removal column by way of the pressure regulator and an entry valve; and a gas vent pipe communicating the removal column with a supply destination by way of an outlet valve; an inert gas delivery pipe and purge gas exhaust pipe respectively provided so as to split off from the supply pipe at an upstream side of the pressure regulator; and heating means provided on the removal column.

Another apparatus for removing siloxanes from a silicon compound gas according to the present invention comprises a removal column filled with diatomaceous earth; a pressure regulator provided in communication with a silicon compound gas source by way of a supply pipe; a gas feed pipe provided in communication with the removal column by way of the pressure regulator and an entry valve; and a gas vent pipe communicating the removal column with a supply destination by way of an outlet valve; an inert gas delivery pipe and purge gas exhaust pipe respectively provided so as to split off from the supply pipe at an upstream side of the pressure regulator; and heating means provided on the inert gas delivery pipe.

Another apparatus for removing siloxanes from a silicon compound gas according to the present invention comprises a removal column filled with diatomaceous earth; a pressure regulator provided in communication with a silicon compound gas source by way of a supply pipe; a gas feed pipe provided in communication with the removal column by way of the pressure regulator and an entry valve; and a gas vent pipe communicating the removal column with a supply destination by way of an outlet valve; an inert gas delivery pipe and purge gas exhaust pipe respectively provided so as to split off from the supply pipe at an upstream side of the pressure regulator; and heating means provided on the removal column and on the inert gas delivery pipe.

Any of the above-mentioned apparatus for removing siloxanes from a silicon compound gas according to the present invention may further comprise a bypass pipe line connecting the gas feed pipe at a downstream side of the pressure regulator with the gas vent pipe at a downstream side of the outlet valve, the bypass pipe line being provided with a valve.

With the method and apparatus for removing siloxanes to purify silicon compound gases according to the present invention as described above, diatomaceous earth which can be economically obtained is used as a removal agent, this diatomaceous earth being thermally activated by heating to a temperature of at least 150° C. and preferably 250–450° C. while feeding inert gas so as to eliminate the water content in the diatomaceous earth to extremely minute quantities, thereby enabling siloxane to be effectively captured and reducing the content of siloxane which should preferably not be contained in silicon compound gases to extremely minute amounts (a few ppb). Additionally, low temperatures of below the ice point (0° C.) are not required, and removal capabilities exceeding those of conventional removal methods can be achieved even under operation at normal environmental temperatures. Consequently, it is possible to supply high-purity silicon compound gases such as monosilane and disilane to required areas of application, thus enabling the production of high-quality products especially in the field of semiconductor production.

Next, as a method for analyzing silicon compound gases for minute quantities of siloxanes in order to evaluate the quality of semiconductor production gases purified by the above-mentioned removal means, the present invention offers a method for analyzing a silicon compound gas for siloxane content according to the present invention comprising steps of preheating a sample collection tube; feeding the silicon compound gas into the sample collection tube to collect the silicon compound gas after preheating; cooling the sample collection tube to a temperature less than the boiling point of siloxane; gradually raising the temperature of the sample collection tube while simultaneously drawing the silicon compound gas from the sample collection tube into a mass spectrometer; and measuring the siloxane content with the mass spectrometer.

Another method for analyzing a silicon compound gas for siloxane content according to the present invention comprises steps of preheating a sample collection tube; cooling the sample collection tube to a temperature less than the boiling point of siloxane after preheating; feeding the silicon compound gas into the sample collection tube to collect the silicon compound gas while maintaining the temperature at less than the boiling point of siloxane; and gradually raising the temperature of the sample collection tube while simultaneously drawing the silicon compound gas from the sample collection tube into a mass spectrometer to measure the siloxane content.

In each of the above-mentioned analysis methods, the preheating temperature should preferably be at least 100° C. Additionally, the cooling temperature should preferably be within the range of −15 to −144° C.

Furthermore, the analysis effects can be improved by forming the sample collection tube of stainless steel. Additionally, the sample collection tube can comprise a stainless steel tube filled with at least one type of filler chosen from among stainless steel filler and glass filler.

An apparatus for carrying out the above-mentioned analysis method of the present invention comprises a valve cage having six pipe mouths arranged along a circumference thereof in the order of a pipe mouth communicating with a silicon compound gas source, a pipe mouth communicating with one side of a sample collection tube provided with cooling means and heating means, a pipe mouth communicating with a mass spectrometer, a pipe mouth communicating with a carrier gas source, a pipe mouth communicating with the other side of the sample collection tube, and a pipe mouth connected to one end of a gas discharge pipe, the other end of which is open to the external atmosphere; and a selector valve element fitted inside the valve cage in airtight fashion such as to be capable of rotating in order to switch between different pipe lines, the selector valve element having six communicating ports positioned such as to be capable of coming into conjunction with the six pipe mouths provided in the valve cage by rotational switching, adjacent pairs of the communicating ports being connected so as to form three pairs of pipe lines; wherein rotation of the selector valve element in the valve cage enables switching in sequence between a sample collecting state for feeding silicon compound gas into a sample collection tube and collecting siloxane by condensation, and an analysis state for vaporizing the collected siloxane and drawing them into a mass spectrometer for analysis.

The siloxane content analyzing method according to the present invention separates siloxanes from the silicon compound gases which are being analyzed as described above, by separating the components due to the differences in their characteristic boiling points without requiring the use of a column using a separating agent as in conventional methods, and adequately preheats the sample collection tubes and exhausts them with inert gas so as to remove the water content before sample collection, as a result of which there is no influence due to the temperature during separation such as fluctuations in the separated quantity as in conventional methods, thereby enabling the separation of components to be performed extremely accurately to make possible precise analysis of the siloxane content. Additionally, the detection of minute quantities of siloxanes to a few ppb which are not detectable by conventional methods is possible, which can be extremely effectively employed for the quality control of high-purity material gases for semiconductor production having extremely minute impurity content which will become more and more necessary in the future.

Furthermore, an analysis apparatus used for this analysis method uses a six-position selector valve which enables connections to be made between a sample gas source, a sample collection tube, a mass spectrometer, a carrier gas source and a gas discharge pipe for discharge into the atmosphere as needed, so that it is possible to switch in sequence between a sample collection state and an analysis state by switching the pipe line, thereby enabling appropriate analyses to be performed by means of simple operations.

BRIEF DESCRIPTION OF THE DRAWINGS

FIG. 9 is a system diagram for a mass analysis step of the analysis apparatus according to the present invention.

DESCRIPTION OF PREFERRED EMBODIMENTS OF THE INVENTION

Figure 1:
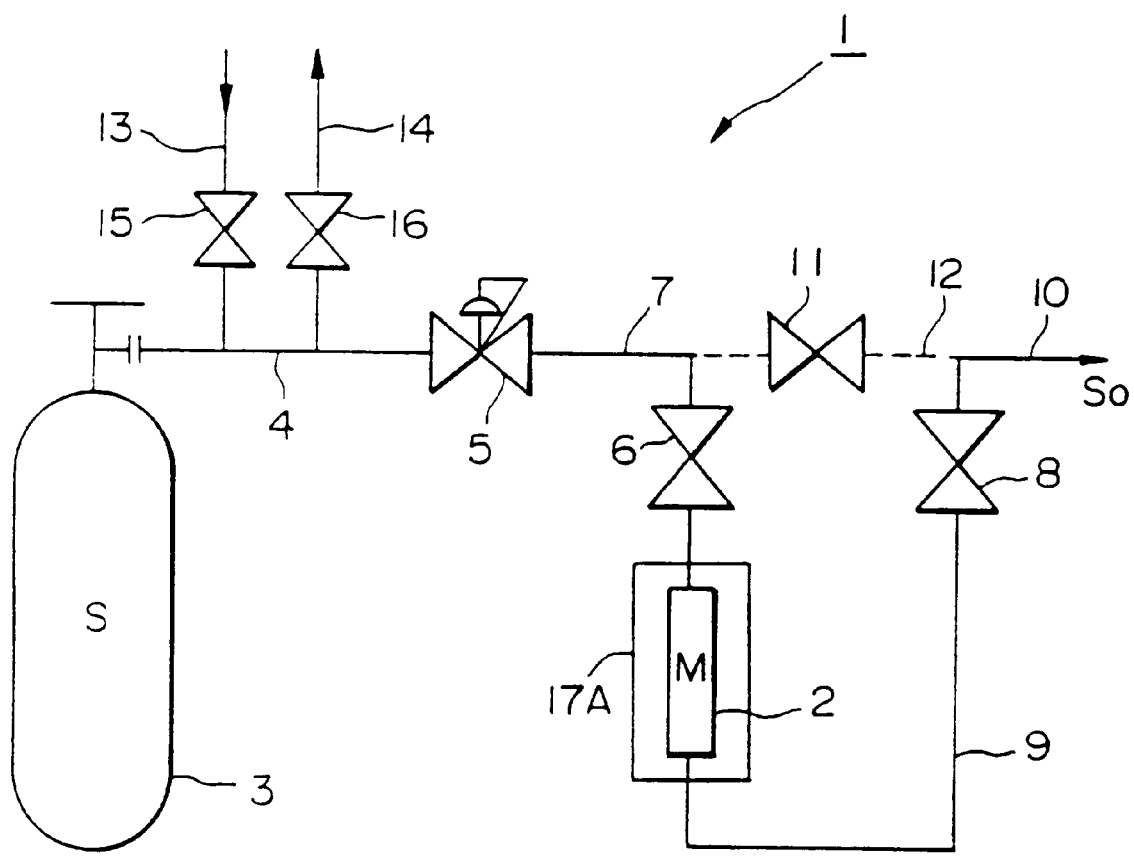
FIG. 1 is a system diagram of a first embodiment of a siloxane removal apparatus according to the present invention.
Figure 2:
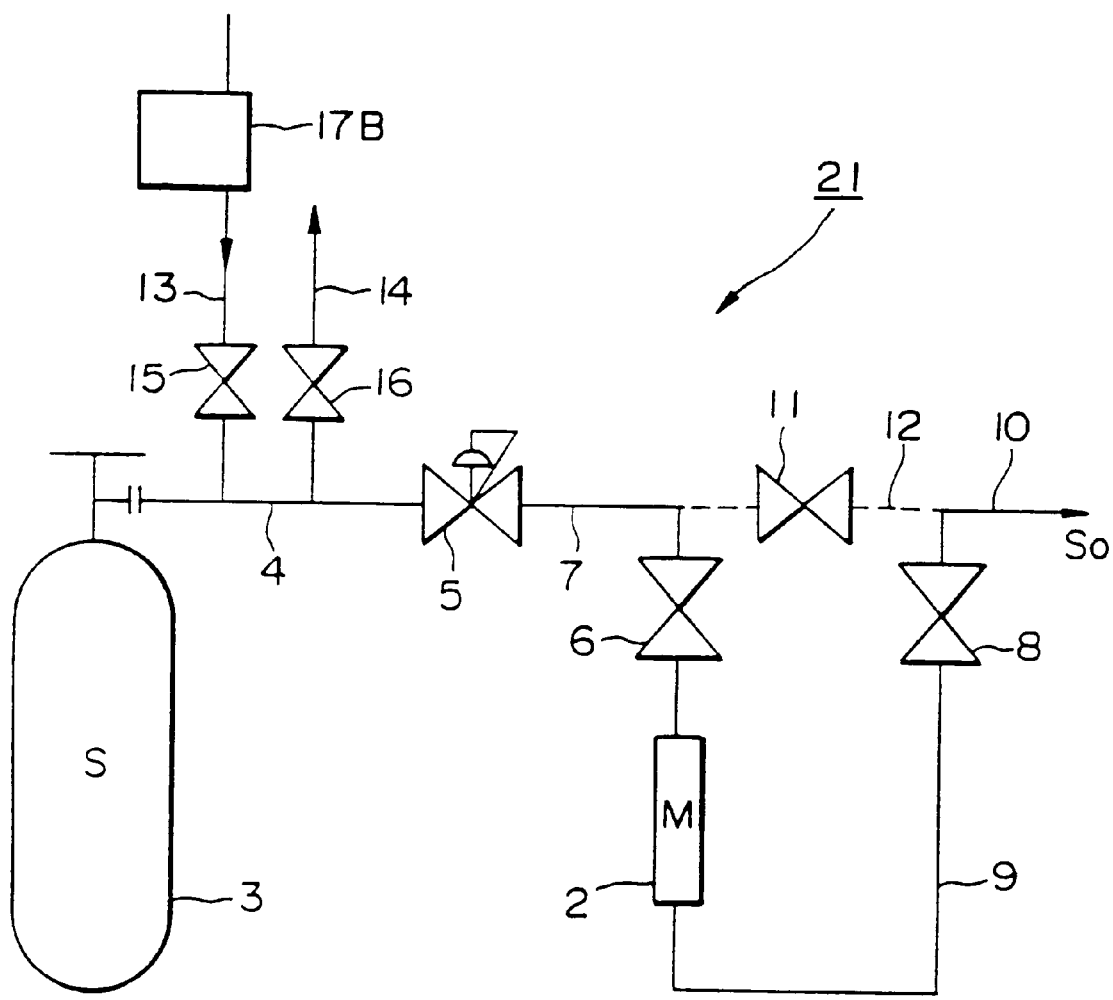
FIG. 2 is a system diagram of a second embodiment of a siloxane removal apparatus according to the present invention.

FIGS. 1 and 2 show examples of embodiments of the apparatus for removing siloxanes according to the present invention. In these drawings, reference numeral 1 denotes a removal apparatus according to the present invention, which comprises a removal column 2 composed of stainless steel or the like and filled with diatomaceous earth M, a supply pipe 4 connected to a storage container 3 and extending to a pressure regulator 5 for supplying the removal column 2 with a silicon compound gas source S stored in the storage container 3, a gas feed pipe 7 connected to the pressure regulator 5 and communicating with the removal column 2 via an entry valve 6, a gas vent pipe provided with an outlet valve 8 for venting gas treated in the removal column 2, and a delivery pipe 10 connected to the outlet valve 8 for delivering the treated gas to a location of use. Additionally, a bypass pipe line 12 having a valve 11 for bypassing the removal column 2 is provided so as to connect the downstream side of the pressure regulator 5 of the gas feed pipe 7 with the downstream side of the gas vent pipe 9.

Also, the removal apparatus 1 of the present invention is provided with an inert gas delivery pipe 13 which branches from the supply pipe 4 on the upstream side of the pressure regulator 5, and a purge gas exhaust pipe 14 for purge-cleansing the inside of the supply pipe 4. Reference numerals 15 and 16 denote valves respectively provided on the inert gas delivery pipe 13 and the purge gas exhaust pipe 14.

Furthermore, the removal apparatus of the present invention provided with this piping system is provided with heating means for activating the diatomaceous earth M filled in the removal column 2. In the removal apparatus 1 of the first embodiment as shown in FIG. 1, the heating means is provided in the form of a heating means 17A such as a heater which surrounds the removal column 2. In the removal apparatus 21 of the second embodiment shown in FIG. 2, the heating means 17B such as a heater is provided on the inert gas delivery pipe 13.

Next, a method for removing siloxanes using the removal apparatus 1 of FIG. 1 as described above shall be explained. First, the valve 15 provided in the inert gas delivery pipe 13, the pressure regulator 5 and the entry valve 6 in the gas feed pipe 7, and the outlet valve 8 of the gas vent pipe 9 are all opened, while the valve 16 of the purge gas exhaust pipe 14 and the valve 11 of the bypass pipe line 12 are closed, then an inert gas such as nitrogen gas is fed in from the inert gas delivery pipe 13 through the supply pipe 4 and the gas feed pipe into the removal column 2, and is allowed to flow out through the gas vent pipe 9 and the outlet valve 8. At this time, the diatomaceous earth M loaded into the removal column 2 is heated to at least 150° C., preferably 250–450° C. by means of the heating means 17A provided on the removal column 2. If the temperature is less than 150° C., then the water content in the diatomaceous earth cannot be sufficiently eliminated, as a result of which contact between the silicon compound and the water content produces siloxanes which must be removed. On the other hand, if the temperature exceeds 450° C., then the active groups in the diatomaceous earth M are destroyed.

After purging the diatomaceous earth M with inert gas while heating for approximately 3 hours, the heating with the heating means 17A is stopped while continuing to feed inert gas into the removal column 2, so as to cool the diatomaceous earth M to a temperature of between 60-0° C., and the valve 11 is opened in order to purge the bypass pipe line 12 with inert gas as well. Subsequently, the pressure regulator 5, the entry valve 6, the outlet valve 8 and the valve 11 of the bypass pipe line 12 are all closed, and the valve 15 is also closed to shut off the supply of inert gas. Then the valve 16 is opened and a vacuum pump (not shown in the drawing) connected to the purge gas exhaust pipe 14 is driven so as to remove components of air which should preferably not remain within the piping of the supply pipe 4 which connects the storage container 3 and the pressure regulator 5.

After completing the preparatory operations described above, the valves 11, 15 and 16 are closed, while the pressure regulator 5, entry valve 6 and outlet valve 8 are opened so that a silicon compound gas S as silane ($SiH_4$) to be processed which is loaded into the storage container 3 is fed through the supply pipe 4 and the gas entry pipe 7 into the removal column 2. The infed silicon compound gas S contacts the diatomaceous earth M which has been treated for activation under the above-described conditions so as to effectively capture siloxanes, after which the silicon compound gas $S_0$ in which the content of siloxanes has become minute (a few ppb) is let out through the gas vent pipe 9 and through the valve 8 so as to be delivered to an area of use by way of the delivery pipe 10.

In the removal apparatus 21 according to the second embodiment as shown in FIG. 2, the heating means for heating and activating the diatomaceous earth M is provided as a heating means 17B which is provided on the inert gas delivery pipe 13 instead of on the removal column 2 as in the removal apparatus of FIG. 1. With regard to the operation, the heating means 17B should be operated in the same manner and at the same time as the heating means 17A of FIG. 1. The other operations are identical to those explained with reference to the removal apparatus 1 of FIG. 1 as described above, and therefore shall be omitted.

While this second embodiment requires a longer heating time because the diatomaceous earth M is not directly heated such as with the heating means 17A of the first embodiment shown in FIG. 1, but is instead heated by means of the heated inert gas; however, this arrangement enables the diatomaceous earth M to be heated evenly and enables uniform activation, while also lengthening the lifetime of the diatomaceous earth. Furthermore, it is also possible to have both the heating means 17A surrounding the removal column 2 such as in the removal apparatus 1 of FIG. 1, and the heating means 17B provided on the inert gas delivery pipe 13 such as in the removal apparatus 21 of FIG. 2. In this case, the heating operation for activation is able to be performed more efficiently.

Figure 3:
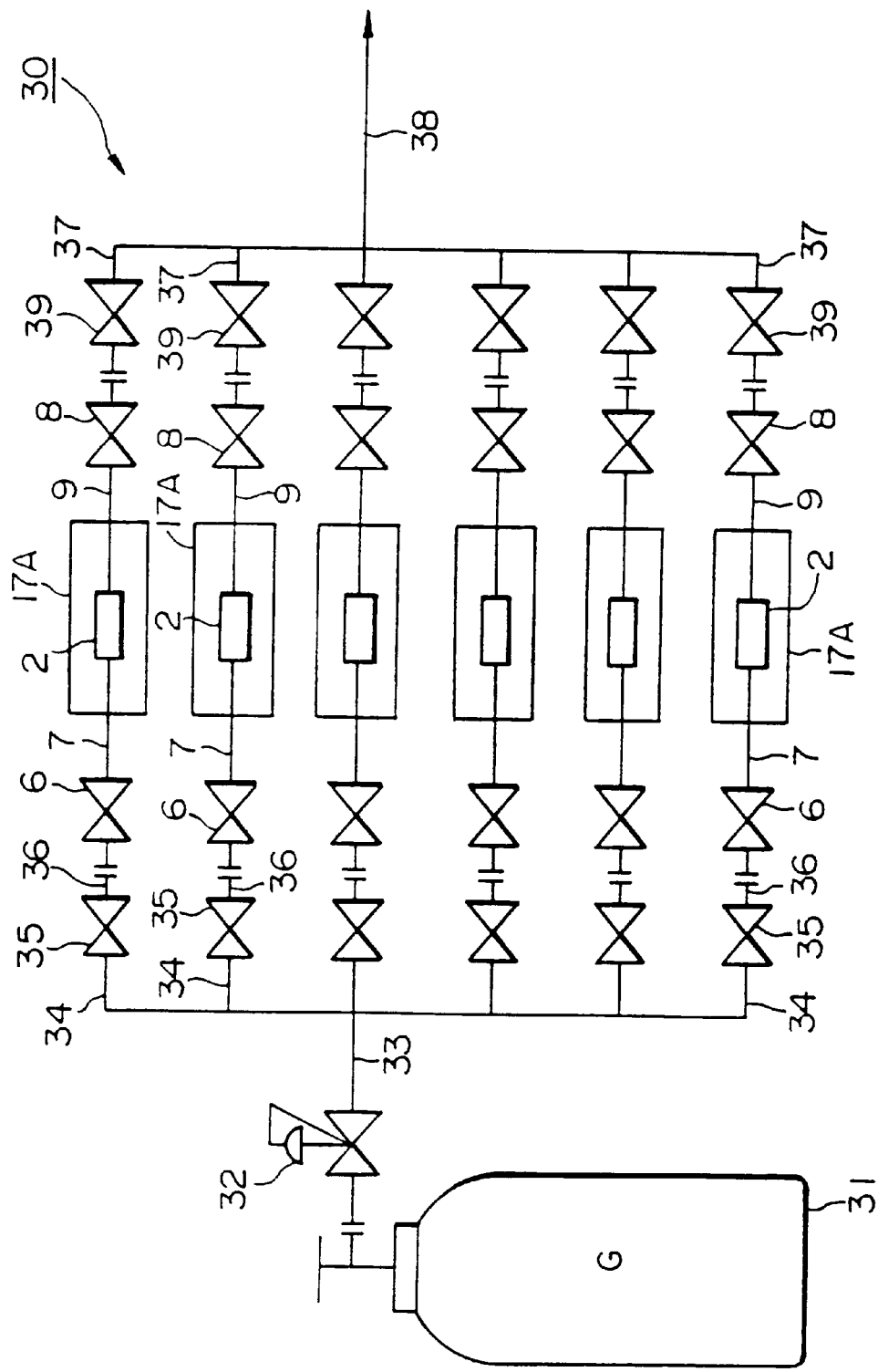
FIG. 3 is a system diagram of an embodiment of a thermal activation apparatus for a siloxane removal column according to the present invention.
Figure 4:
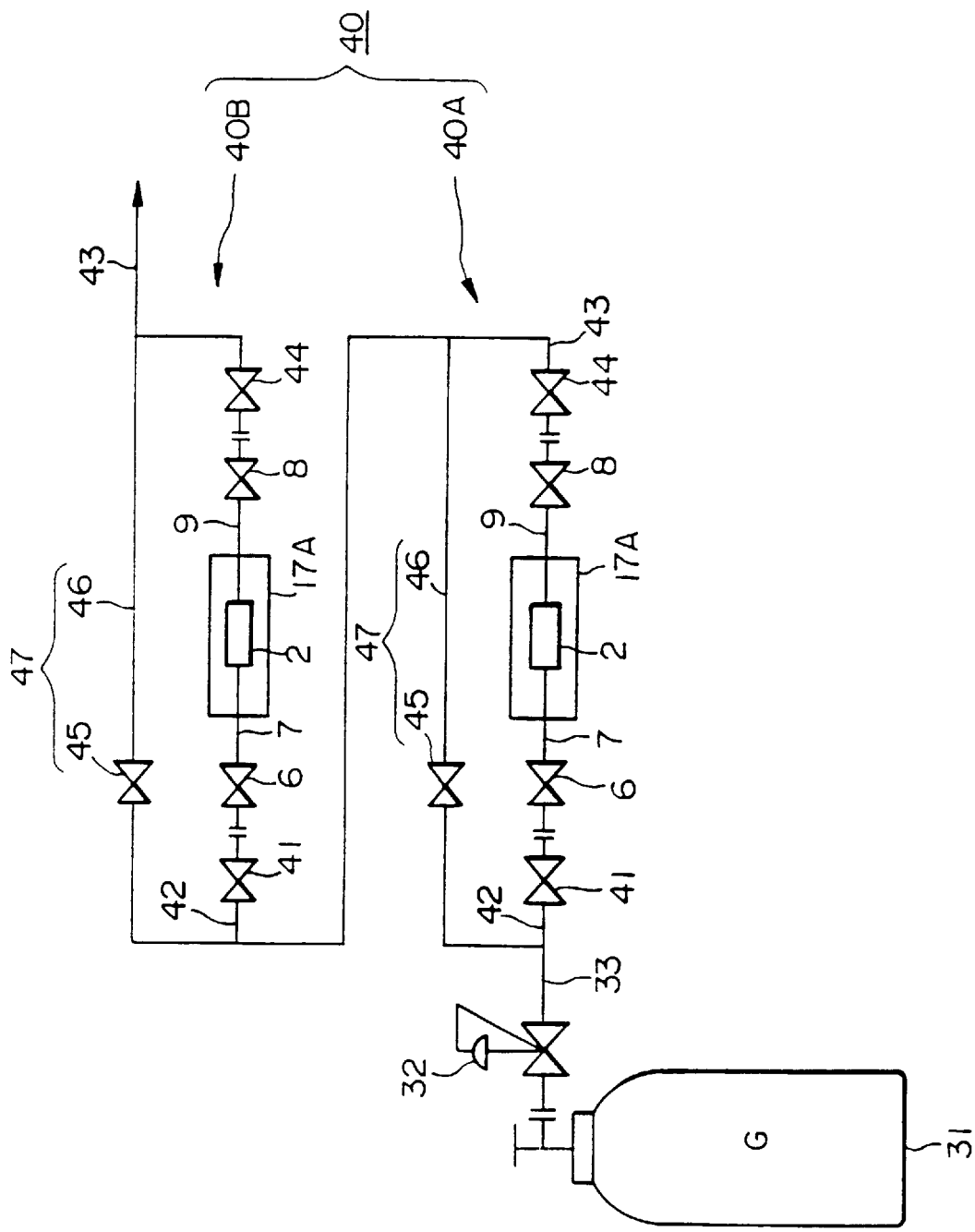
FIG. 4 is a system diagram of another embodiment of a thermal activation apparatus for a siloxane removal column according to the present invention.

Next, thermal activation apparatus exclusively for the purposes of activation, for activating the removal column 2 independently of the removal apparatus 1 and 21, to be used in the method for removing siloxanes according to the present invention shall be explained by means of the two examples shown in FIGS. 3 and 4. The removal column according to this embodiment does not have equipment for thermal activation of diatomaceous earth M, and is conveniently and effectively used simply by attachment to a gas delivery system at the time of use of the gas at a location of use of the gas which is equipped only with a gas delivery installation used for production of semiconductors.

FIG. 3 shows a system diagram of an embodiment of an apparatus for thermal activation of diatomaceous earth M loaded into a removal column used for removal of siloxanes according to the present invention. The removal column 2 is composed of a stainless steel tubular body as described in connection with FIGS. 1 and 2, and is filled with diatomaceous earth M. A heating means 17A such as an electrical heater is provided such as to surround the outer circumference of the removal column 2. This removal column 2 is connected with a gas entry pipe 7 having an entry valve 6, and a gas vent pipe 9 having an outlet valve 8. The embodiment of FIG. 3 is an apparatus 30 which comprises a plurality of removal columns 2 as described above which are arranged in parallel fashion, and are detachably connected to a gas cylinder 31 containing an inert gas source G of an inert gas such as nitrogen gas, argon gas or helium gas.

This thermal activation apparatus 30 has a supply pipe 33 provided with a pressure regulator 32 detachably connected to a gas cylinder 31 containing an inert gas source G (such as nitrogen gas, argon gas or helium gas), and has a plurality of feed branch pipes 34 which branch in parallel and are connected to the downstream side of the pressure regulator 32. These feed branch pipes 34 are each provided with a gate valve 35, and each gate valve 35 is also joined to a connecting pipe 36 which detachably connects to the entry valve 6 of the removal column 2. On the other hand, a removal column 2 is connected to each feed branch pipe 34 via a connecting pipe 36, each removal column 2 being provided with a vent pipe 9 through which inert gas for activating the diatomaceous earth M is exhausted by means of an outlet valve 8. Adjoining each outlet valve 8 is a discharge branch pipe 37 for discharging the inert gas to the external atmosphere, these discharge branch pipes 37 being arranged in parallel fashion corresponding to the feed branch pipes 34, and converging on a pipe 38. Each discharge branch pipe 37 is provided with a gate valve 39. Additionally, each discharge branch pipe 37 is provided with couplers for detachably coupling a vent pipe 9 of a removal column 2 for thermal activation.

In this apparatus 30, a plurality of removal columns 2 requiring thermal activation are provided between respective feed branch pipes 34 and corresponding discharge branch pipes 37. By opening the entry valve 6 and the outlet valve 8 provided in each removal column 2 and opening the gate valve 35 provided in each feed branch pipe 34 and the gate valve 39 provided in each discharge branch pipe 37, the inert gas G such as helium contained in the gas cylinder 31 is allowed to flow through the pressure regulator 32 into each removal column 2 under a pressure of 1–3 kg.f/cm². Simultaneously, the heating means 17A provided in each removal column 2 is activated so as to heat the diatomaceous earth M inside the removal column 2 to at least 150° C., and preferably to 250–450° C.

After performing the above-described procedure for approximately 2–3 hours, the heating is stopped, and inert gas G is fed to cool the diatomaceous earth M to room temperature (60-0° C.). Subsequently, the entry valves 6 and outlet valves 8 of the removal columns 2 are closed, and the gate valves 35 and 39 provided in the feed branch pipes 34 and the discharge branch pipes 37 are closed, so as to shut off the inflow of inert gas G into the removal columns 2 through the feed branch pipes 34. Additionally, the removal columns 2 attached to the feed branch pipes 34 and the discharge branch pipes 37 are detached from the branch pipes 34 and 37 at the upstream side of the entry valves 6 and the downstream side of the outlet valves 8. While the diatomaceous earth M was cooled by feeding inert gas in the above explanation, the entry valves 6 and the outlet valves 8 of the removal columns 2 can be closed without feeding any further inert gas into the removal columns 2, and the diatomaceous earth M can be let stand for natural cooling.

The activated removal columns 2 obtained in this manner can be effectively used by delivery to locations of use such as semiconductor factories which use silicon compound gases. This thermal activation apparatus 30 increases the work efficiency because it enables the activation of a plurality of removal columns filled with diatomaceous earth with a single operation. Additionally, since the removal columns 2 are individually separable, it is possible to perform different activation procedures according to the grain sizes or filled amounts of diatomaceous earth M in different types of removal columns 2 which may have different uses. Additionally, since each removal column 2 is detachable without any dependence on the other removal columns 2, the removal columns 2 in which activation has been completed can be removed or new removal columns 2 can be attached for activation even while other removal columns are undergoing the activation procedure, without affecting the activation procedure.

FIG. 4 shows another embodiment of the thermal activation apparatus for removal columns 2 filled with diatomaceous earth M, which is different from the thermal activation apparatus 30 of FIG. 3 in that whereas the plurality of removal columns 2 to be activated are connected in parallel in FIG. 3, the plurality of removal columns 2 to be activated are connected in series for thermal activation in the thermal activation apparatus 40 of FIG. 4. This embodiment shall be described below. The components which are identical to those of FIG. 3 are given the same reference numerals, and there detailed descriptions shall be omitted.

That is, this thermal activation apparatus 40 has a feed branch pipe 42 provided with a gate valve 41 connected to a supply pipe 33 having a pressure regulator 32 and joined with a gas cylinder 31 which contains an inert gas source G. The other side of the branch pipe 42 has a gas feed pipe 7 provided with an entry valve 6 of a removal column 2 detachably connected thereto. On the other hand, a discharge branch pipe 43 which is detachably connected with a gas vent pipe 9 provided with an outlet valve 8 of the removal column 2 is provided in correspondence to the feed branch pipe 42, and has a gate valve 44. Furthermore, a bypass pipe line 47 which connects an upstream side of the gate valve 41 provided in the feed branch pipe 42 with the downstream side of the gate valve 44 provided in the discharge branch pipe 43 by means of a pipe 46 via a valve 45 is provided to form a first thermal activation apparatus 40A.

Additionally, a second thermal activation apparatus 40B provided with a feed branch pipe 42 having a gate valve 41, a discharge branch pipe 43 having a gate valve 44, and a bypass pipe line 47 connecting the upstream side of the gate valve 41 with the downstream side of the gate valve 44 by means of a pipe 46 via a valve 45, identical to the first thermal activation apparatus 40A is also formed. The discharge branch pipe 43 of the first thermal activation apparatus 40A is joined with the feed branch pipe 42 of the second thermal activation apparatus 40B in order to connect these apparatus in series. It is possible to serially connect an arbitrary number of thermal activation apparatus in the following manner.

In this embodiment, when a plurality of removal columns 2 are to simultaneously undergo thermal activation, the bypass valve 45 is closed and the other valves, i.e. the gate valves 41 and 44, the entry valve 6 and the outlet valve 8 are opened while feeding inert gas into the removal columns 2 for thermal activation. When one removal column 2 is to undergo thermal activation while another removal column 2 is being detached or attached, the thermal activation apparatus being detached or attached, for example the first apparatus 40A, should be prepared by closing the gate valves 41 and 44, the entry valve 6 and the outlet valve 8 of the first apparatus 40A, and opening the bypass valve 45 of this apparatus 40A. Then, the inert gas G will flow through the bypass pipe line 47 of the first apparatus 40A to the feed branch pipe 42 of the second apparatus 40B, pass through the gas entry pipe 7 and be fed into the removal column 2, then expelled from the system through the gas vent pipe 9 and the discharge branch pipe 44. During this time, the attachment or detachment work on the removal column 2 of the first apparatus 40A can be performed as suitable, and the work can be done freely without affecting the other thermal activation procedures (in the second apparatus 40B).

Similar to the thermal activation apparatus 30 shown in FIG. 3, the apparatus 40 of this embodiment allows for simultaneous thermal activation of the plurality of removal columns 2 and is therefore efficient, while also enabling independent activation of each removal column 2, thereby allowing attachment or detachment of removal columns 2 without affecting the thermal activation of others, so as to markedly improve the work efficiency. Furthermore, since the removal columns 2 can be filled with diatomaceous earth M in various grain sizes and amounts, thermal activation of each removal column 2 under mutually differing optimum conditions is possible, so that the range of applications is extremely broad. They can be used extremely easily and effectively, particularly in the field of use of silicon compound gases in semiconductor production factories. Of course, the removal columns 2 filled with diatomaceous earth used for the thermal activation apparatus shown in FIGS. 3 and 4 can also be used by attachment to the siloxane removal apparatus shown in FIGS. 1 and 2 as well.

EXAMPLE 1

As Example 1 of a siloxane removal method according to the present invention, an experiment was conducted to remove the siloxanes in monosilane ($SiH_4$) which is a silicon compound gas using the siloxane removal apparatus 1 shown in FIG. 1.

A stainless steel removal column 2 having a capacity of 30 cc was filled with diatomaceous earth M having a grain size of 80 mesh. The entry valve 6 and outlet valve 8 were closed and these were joined respectively to the pressure regulator 5 and the delivery pipe 10 with the removal column 2 attached therebetween. Then, the removal column 2 was heated to a temperature of 350° C. with the heating means 17A, while simultaneously opening the entry valve 6, outlet valve 8, pressure regulator 5 and the valve 15 of the inert gas delivery pipe 13 (closing the bypass valve 11 and valve 16 of the purge gas exhaust pipe 14), while feeding nitrogen gas as an inert gas to the removal column 2 at a rate of 200 cc per minute, and this condition was maintained for approximately three hours.

Subsequently, the entry valve 6, outlet valve 8, pressure regulator 5 and the valve 15 of the inert gas delivery pipe 13 were closed, and after confirming the closure of the bypass valve 11, the valve 16 of the purge gas exhaust pipe 14 was opened. Then the vacuum pump (not shown in the drawing) connected to the pipe 14 was driven to evacuate the gas from the supply pipe 4 connecting the storage container 3 with the pressure regulator 5. During this time, the temperature of the removal column 2 was cooled with external cool air to room temperature of less than 60° C. Then, the valve 16 of the purge gas exhaust pipe 14 was closed, and after confirming the closure of the bypass valve 11 and the valve 15 of the inert gas delivery pipe 13, the valve of the storage container 3 was opened. Thereafter, the pressure regulator 5, the entry valve 6 and the outlet valve 8 were opened in sequence so as to lead the monosilane gas ($SiH_4$) from the storage container 3 to the removal column 2 to come into contact with the activated diatomaceous earth M.

Figure 5:
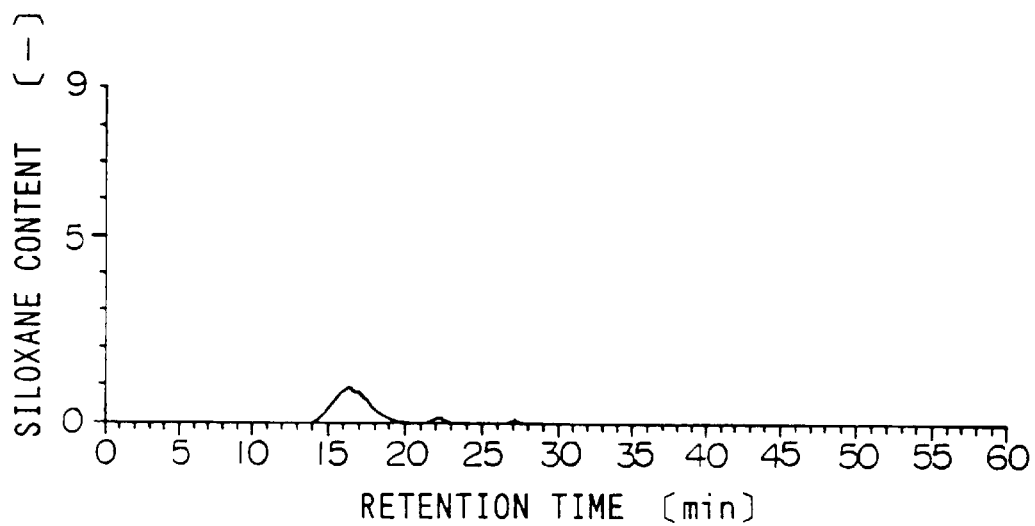
FIG. 5 is a graph showing the siloxane content of monosilane after processing the monosilane in accordance with the present invention.

The purified monosilane $S_0$ which has contacted the activated diatomaceous earth M and been let out through the gas vent pipe 9 according to the method of the present invention was collected through the outlet valve 8, and the content of siloxanes in this silane was measured. The results are shown in the graph of FIG. 5. The scales of the content shown in the vertical axis of the graph are relative values which are used for the sake of convenience in order to simplify quantitative determinations.

The analysis method which was used was the analysis method developed for the present invention which shall be described below. A standard amount (1000 cc) of the test sample gas was collected and this was cooled to −110° C. using cooling means such as liquid nitrogen (boiling point: −196° C.), then the temperature was gradually raised in order to separate monosilanes (boiling point: −112° C.) and siloxanes (boiling point: −15° C.) due to the differences in their boiling points, and the samples were analyzed by using a mass spectrometer (condensation vaporization method).

Figure 6:
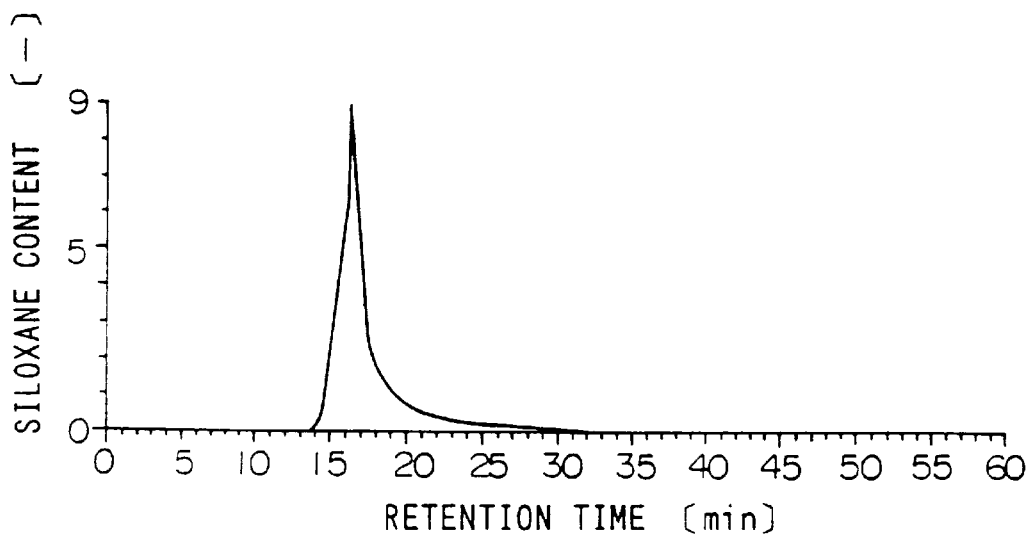
FIG. 6 is a graph showing the siloxane content in a monosilane raw material used in the present invention.

Additionally, for the purposes of comparison, FIG. 6 shows a graph of the measurement of the siloxane content in raw monosilane S stored in the storage container 3 used in the removal method of the present invention. The amount of the test sample gas collected was 1000 cc, the same as above, and the analysis method was also the same. The scales for the content indicated on the vertical axis are the same as in FIG. 5, and the scales were callibrated according to the same standards as in FIG. 5.

As is clear upon comparison of FIGS. 5 and 6, the amount of siloxanes in the monosilane $S_0$ which was purified by incorporating into the removal apparatus of the present invention shown in FIG. 5 was reduced approximately below 1/10 of the amount of siloxanes in the raw monosilane that was not purified shown in FIG. 6. This makes it clear that the siloxane removal effects are remarkable. The concentration of siloxanes in the raw monosilane S prior to purification was approximately 60 ppb.

Additionally, while Example 1 has been described for an example wherein the removal method using the removal apparatus shown in FIG. 1 was used, the same effects were able to be obtained using a removal apparatus 21 as shown in FIG. 2.

EXAMPLE 2

Next, an experiment was conducted on the effects of treatment temperature on the siloxane removal ability of the thermally activated diatomaceous earth M as Example 2.

Figure 7:
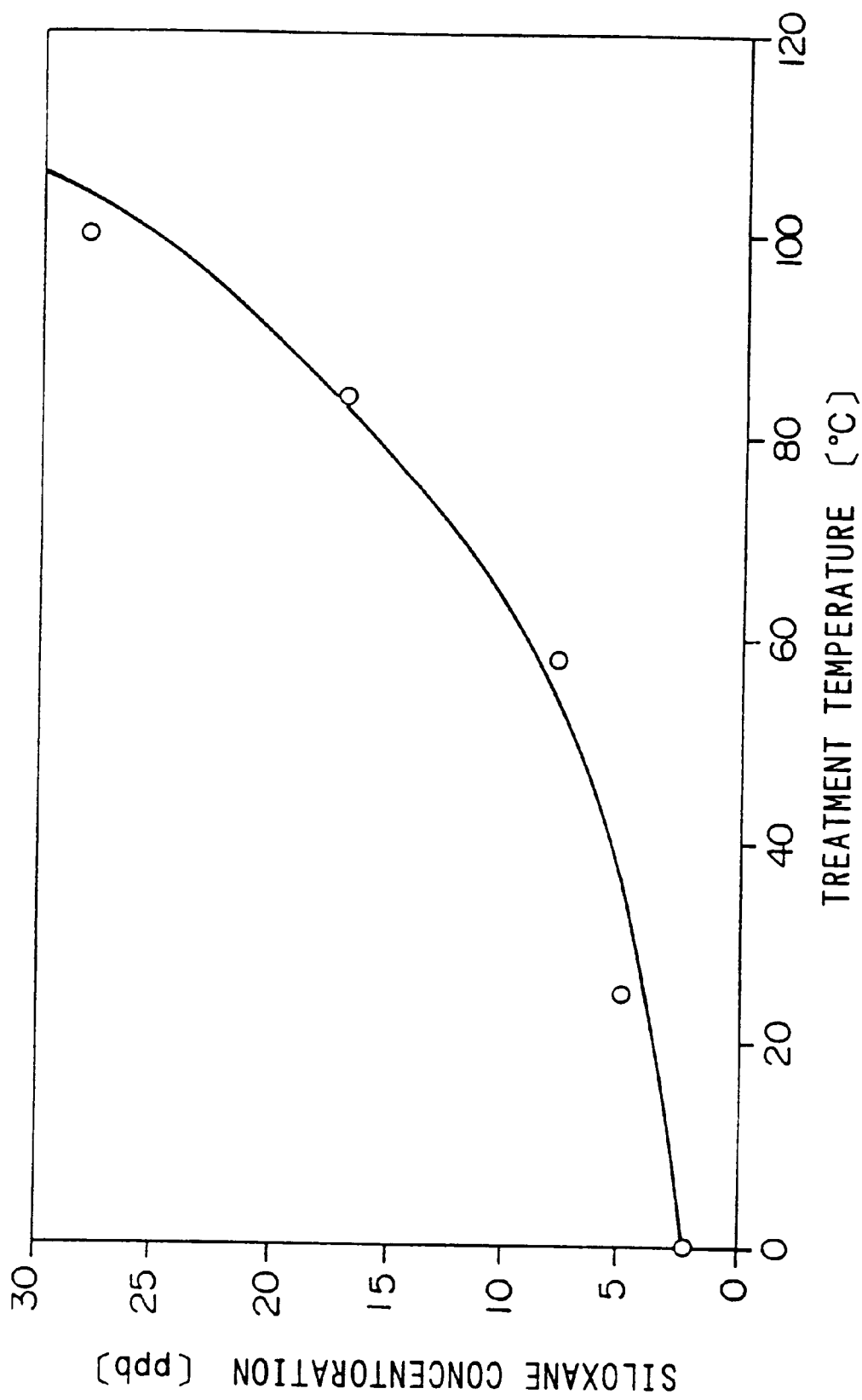
FIG. 7 is a graph showing the siloxane removal effects depending on the driving temperature in a removal method according to the present invention.

After thermally activating the diatomaceous earth M inside a removal column 2 using the same methods as described for Example 1, the temperature inside the removal column 2 was varied over a range of 0–100° C. while feeding raw monosilane S (siloxane concentration: approximately 60 ppb) into the removal column 2, and the change in the siloxane concentration in the purified monosilane $S_0$ was analyzed. The results are shown in the graph of FIG. 7 which indicates the change in the siloxane concentration (ppb) depending on the removal treatment temperature (° C.). The analysis method which was used was the same as the analysis method described for Example 1.

As is clear from FIG. 7, the siloxane removal effects according to the method of the present invention are low at high temperatures, and the removal effects rise as the temperature becomes lower. In particular, the graph demonstrates that siloxanes can be removed to a concentration of less than 10 ppb when the temperature is less than 60° C., and further can be removed to a concentration of 2 ppb at a temperature of 0° C. Accordingly, the method of the present invention enables adequate removal of siloxanes at room temperature, and activates siloxane removal effects greater than with conventional methods at room temperature operation, without operation at low temperatures of less than the freezing point (0° C.) as in conventional methods. In particular, the present invention contributes to increases in the workability during semiconductor production, and improvements in quality.

While the above examples describe removal of siloxanes from monosilane, the present invention is not necessarily restricted thereto, and can be used for removal of siloxanes from other silicon compound gases such as disilane ($Si_2H_6$), halides thereof, silicon tetrafluoride ($SiF_4$) and silicon tetrachloride ($SiCl_4$) as well.

Next, an embodiment for a case of analyzing a silicon compound gas for the content of siloxanes after removal of the siloxanes in the above manner, for example, according to an analysis method and analysis apparatus of the present invention shall be described.

Figure 8:
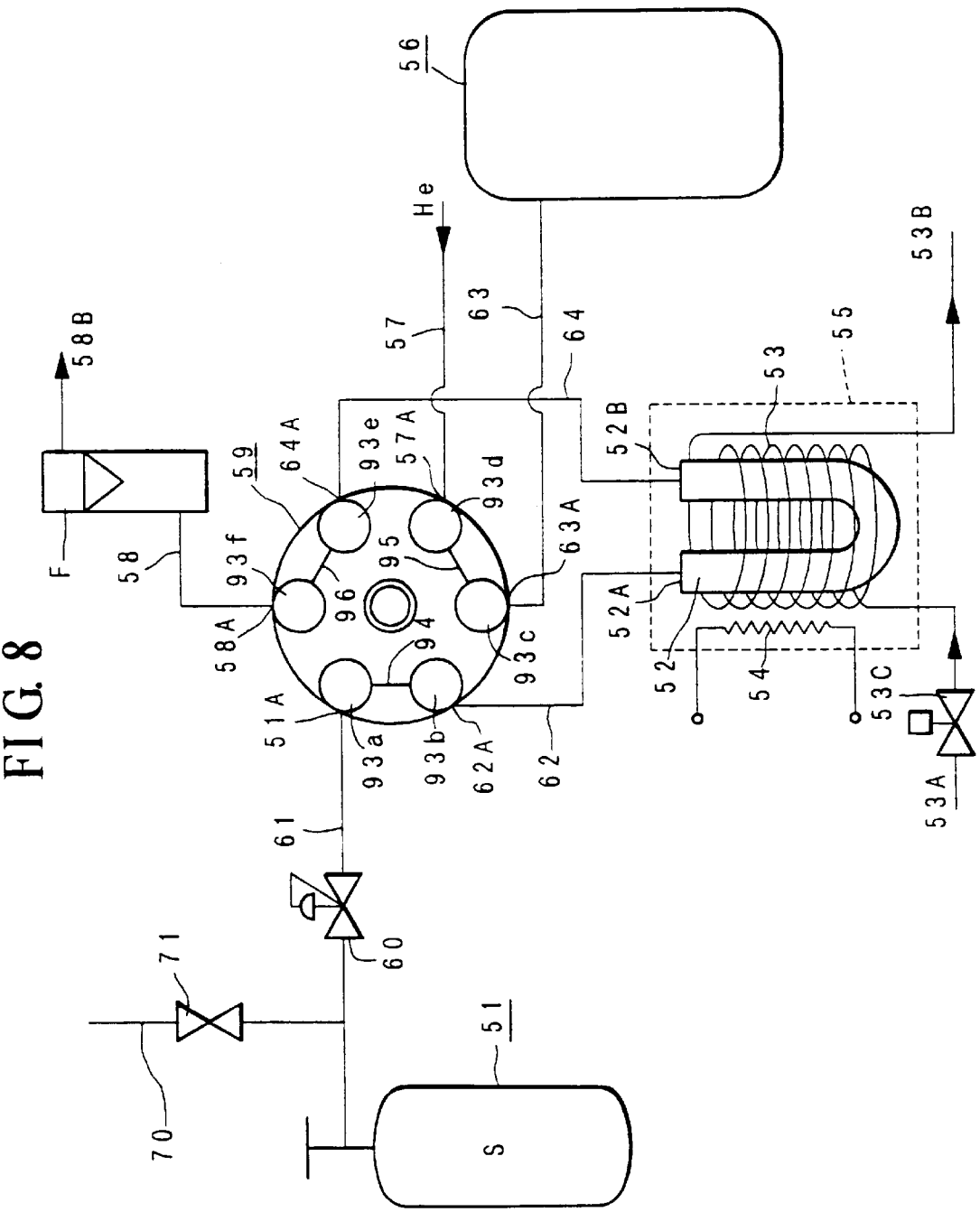
FIG. 8 is a system diagram for a sample collecting step of the analysis apparatus according to the present invention.

FIGS. 8 and 9 are schematic system diagrams for explaining an example of an embodiment of a method for analyzing the siloxanes in silicon compound gases according to the present invention. In FIGS. 8 and 9, reference numeral 51 denotes a storage container filled with a silicon compound gas S which is the gas to be analyzed, and reference numeral 52 is a stainless steel or glass sample collection tube, which should preferably contain fillings such as stainless steel chips or glass beads for effectively transmitting heat which is transferred during cooling or heating. Reference numeral 53 denotes a cooler for cooling the sample collection tube 52, to which a low-temperature liquefied gas such as liquid nitrogen is supplied as a cooling medium from the pipe 53A via the valve 53C, and is allowed to flow out through the pipe 53B after cooling. Additionally, reference numeral 54 denotes a heater for heating the sample collection tube 52. The sample collection tube 52, cooler 53 and heater 54 should preferably be housed inside an insulating box 55.

Reference numeral 56 denotes a mass spectrometer, reference numeral 57 denotes a carrier gas feed pipe for which communicates with a carrier gas source He containing helium gas for leading the sample gas collected in the sample collection tube 52 to the mass spectrometer 56, and reference numeral 58 denotes a gas exhaust pipe connected via a flow meter F to a detoxication (not shown in the drawing) having a tube end 58B on one side which eliminates poisonous components by expelling them to the external atmosphere. These mechanisms are connected by means of a six-position selector valve 59 so as to be capable of communicating or being shut off depending on the processing step such as the sample collecting step and the analysis step.

Figure 10A:
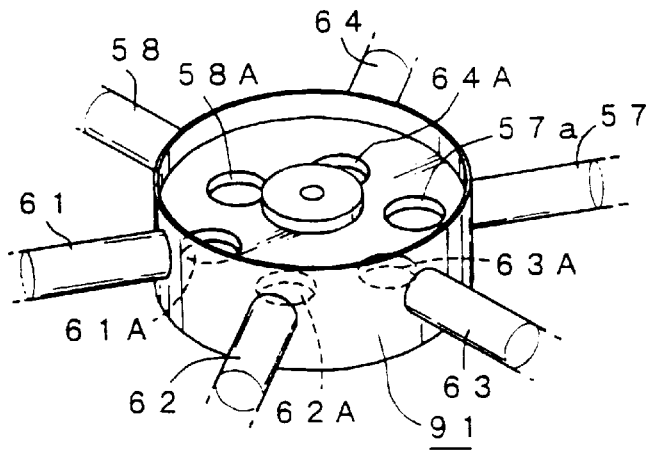
FIG. 10A is an assembly diagram for a six-direction selector valve used for the analysis apparatus according to the present invention, and is a unit diagram of a perspective view showing a valve cage.
Figure 10B:
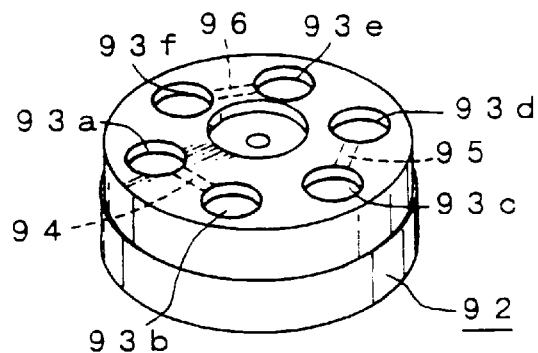
FIG. 10B is an assembly diagram for a six-direction selector valve used for the analysis apparatus according to the present invention, and is a unit diagram of a perspective view showing a valve element.
Figure 10C:
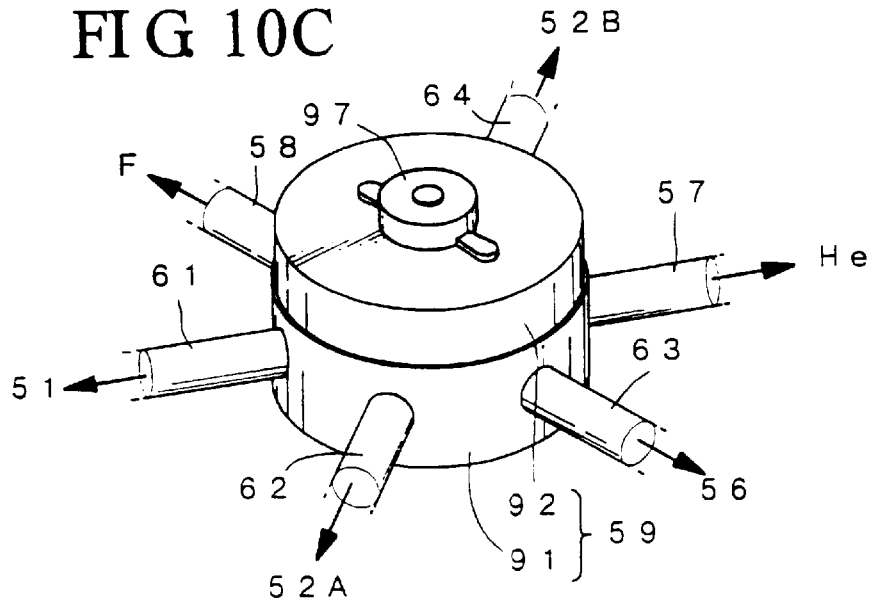
FIG. 10C is an assembly diagram for a six-direction selector valve used for the analysis apparatus according to the present invention, and is a diagram of a perspective view showing a six-direction selector valve assembled by fitting the valve element into the valve cage.

That is, the six-position selector valve 59 is composed of a valve cage 91 and a valve element 92 which fits into the valve cage cage 91 in an airtight manner and such as to be capable of rotating, as shown in FIGS. 10A, 10B and 10C. As shown in FIG. 10A, the valve cage 91 is provided with a pipe mouth 61A of a sample feed pipe 61 having a pressure regulator 60 that is connected to a storage container 51 for a silicon compound gas S, a pipe mouth 62A of a pipe 62 connected to one side 52A of the sample collection tube 52, a pipe mouth 63A of a pipe 63 that is connected to the mass spectrometer 56, a pipe mouth 57A of a carrier gas feed pipe 57 which communicates with the carrier gas source He, a pipe mouth 64A of a pipe 64 connected to the other side 52B of the sample collection tube 52, and another pipe mouth 58A of the gas exhaust pipe 58 having one side 58B communicating with the detoxication unit (not shown in the drawing). These six pipe mouths are arranged in a circle in the above-described order.

Additionally, as shown in FIG. 10B, the valve element 92 which is fitted into the valve cage 91 in an airtight manner and such as to be capable of rotating is provided with six communication ports 93a, 93b, 93c, 93d, 93e and 93f which are arranged on the same circle as the arrangement of the pipe mouths in the valve cage so as to always be in conjunction with the six pipe mouths in the valve cage 91 even when the valve element 92 is in rotary motion. Each of the six communication ports 93 forms a pair with an adjacent communication port, such as to form pairs of 93a–93b, 93c–93d and 93e–93f, which are connected by means of the pipe lines 94, 95 and 96 respectively.

As shown in FIG. 10C, the valve cage 91 and valve element 92 structured in this manner are integrated by fitting the valve element 92 into the valve cage 91 in an airtight manner and such as to be capable of rotating, so as to form a six-position selector valve 59, which connects the equipment shown in FIGS. 8 and 9 by means of a switchable pipe line, thereby constituting an apparatus for analyzing silicon compound gases for siloxanes in accordance with the present invention. Reference numeral 97 denotes a handle for rotating the valve element 92.

A method for measuring the siloxanes in a silicon compound gas using the apparatus of the present invention shall be described. First, the six-position selector valve 59 is set as shown in FIG. 8, so that the communication port 93a of the valve element 92 will be in conjunction with the pipe mouth 61A provided in the valve cage 91 for the feed pipe which connects with the storage container 51 for storing the silicon compound gas S. Then, the other communication ports of the valve element 92 and the pipe mouths of the valve cage 91 will automatically come into conjunction in the following manner: 93b-62A, 93c-63A, 93d-57A, 93e-64A and 93f-58A. Thus, the two flow lines of the storage container 51—sample collection tube 52—flow meter F—discharge to external atmosphere, and carrier gas source He—mass spectrometer 56 are formed.

In this state, helium gas is fed as a carrier gas source He from the carrier gas feed pipe 57 to the mass spectrometer 56. On the other hand, the sample collection tube 52 is heated to a temperature of at least 100° C. by the heater 54, and an inert gas such as helium gas or nitrogen gas is supplied to the sample feed pipe 61 from the pipe 70 via the valve 71, then this inert gas is fed into the sample collection tube 52 and expelled into the external atmosphere through the flow meter F. After adequately heating and cleansing the inside of the sample collection tube 52 in this way, the heating is stopped and a cooling medium such as liquid nitrogen is fed into the cooler 53 through the pipe 53A via the valve 53C, so as to cool the sample collection tube 52. Since the cooling temperature must be such as to enable the siloxanes which are being analyzed to be completely captured, the temperature should preferably be between −15° C. which is the boiling point of siloxane and −144° C. which is the melting point of siloxane. At a temperature of more than −15° C., the siloxane will not condense, and will flow through the sample collection tube 52 while still in a gaseous state and be expelled into the external atmosphere, thus resulting in true measurement values not being obtained. Additionally, at less than −144° C., the siloxane will solidify, so that more time will be required for it to vaporize in the next step of analysis, as well as this being a waste of cooling expenditures.

Subsequently, the valve 71 is closed to shut off the supply of inert gas, while the valve of the storage container 51 is opened so as to feed the silicon compound gas S in the storage container 51 through the pressure regulator 60, the sample feed pipe 61 and the pipe 62 into the sample collection tube 52, then to continue through the pipe 64, the gas exhaust pipe 58, and the flow meter F to the detoxication unit (not shown in the drawings) via the pipe mouth 58B so as to be expelled into the external atmosphere. At this time, the sample collection tube 52 is continually maintained at the above-described cooling temperature. Additionally, at this time, the flow rate of the silicon compound gas S flowing through the sample collection tube 52 is measured by the flow meter F.

After a predetermined amount has flowed through, the six-position selector valve 59 is rotated (for example, in a clockwise direction) to a position such that the communication ports of the valve element 92 and the pipe mouths of the valve cage 91 come into conjunction as follows: 93a-58A, 93b-61A, 93c-62A, 93d-63A, 93e-57A and 93f-64A as shown in FIG. 9. As a result, the two flow lines of the storage container 51—flow meter F—discharge into the external atmosphere, and carrier gas source He—sample collection tube 52—mass spectrometer 56 are formed. Thus, the silicon compound gas which has been fed into the sample collection tube 52 passes through the flow meter F from the storage container 51 and on through the pipe mouth 58B to eliminate the poisonous components at the detoxication unit, after which it is expelled into the external atmosphere. On the other hand, the helium gas which is the carrier gas source He passes through the carrier gas feed tube 57 to the pipe 64 and is fed into the sample collection tube 52, flows from the sample collection tube through the pipe 62 and pipe 63, and is fed to the mass spectrometer 56. Then, the valve 53C is closed so as to shut off the supply of the cooling medium, and the cooling of the sample collection tube 52 is stopped while also starting to operate the heater 54 to heat the sample collection tube 52.

As a result, the components which have condensed and liquefied or frozen and solidified in the sample collection tube 52 during the cooling step are melted or vaporized according to their respective melting points and boiling points due to the rise in temperature. The boiling points and melting points of siloxane and silicon compound gases are listed in Table 1.

TABLE 1

| SUBSTANCE | BOILING POINT (° C.) | MELTING POINT (° C.) |
| --- | --- | --- |
| Siloxane ($H_3Si$—O—$H_3Si$) | −15.0 | −144.0 |
| Monosilane ($SiH_4$) | −111.9 | −185.0 |
| Disilane ($Si_2H_6$) | −14.5 | −132.5 |
| Silane Trichloride ($SiHCl_3$) | +31.8 | −128.2 |
| Silane Dichloride ($SiH_2Cl_2$) | +8.0 | −122.0 |
| Silicon Tetrachloride ($SiCl_4$) | +56.8 | −68.8 |
| Silicon Tetrafluoride ($SiF_4$) | | −95.0 (sublimation) |

As shown in Table 1, the boiling point of siloxane is −15° C., and the boiling points of the other silicon compound gases are lower temperatures or higher temperatures, and the temperatures are different from those of siloxane.

Therefore, the components having boiling points lower than the boiling point of siloxane (−15° C.) are vaporized while the temperature is gradually raised by heating from the cooling temperature of −144° C., before the temperature reaches the boiling point of siloxane, so as to be transported together with the carrier gas He fed into the sample collection tube to the mass spectrometer 56. On the other hand, the components which have boiling points higher than the boiling point of siloxane (−15° C.) remain unvaporized at the temperature of −15° C. at which the siloxane vaporizes, and retain a liquid form. Accordingly, only the condensed fluid of the siloxane which is held inside the sample collection tube 52 begins to be vaporized when a temperature of −10° C. to −15° C. is reached, and this vaporized siloxane is transported together with the carrier gas He fed to the sample collection tube 52 into the mass spectrometer 56.

As a result, the silicon compound gas and the siloxane mixed therein are completely separated and fed into the mass spectrometer 56, so that the amount of siloxane can be measured by a normal analysis operation of the mass spectrometer. Then, the concentration of siloxane contained in the silicon compound gas S can be obtained by calculating the ratio m/M between the volume (m) of the siloxane obtained in this way and the rate of flow (M) of the silicon compound gas S which flowed through the sample collection tube 52 during the sample collection.

In order to collect the silicon compound gas S in the sample collection tube 52 for the above embodiment, the silicon compound gas S was fed into the sample collection tube 52 which was cooled to a predetermined temperature, so as to condense the contained siloxane inside the sample collection tube 52, while measuring the volume of the silicon compound gas S which was fed into the sample collection tube 52. However, the present invention is not necessarily restricted to such an embodiment, and the sample collection can be performed by feeding and collecting the silicon compound gas S at room temperature without cooling the sample collection tube 52 to a low temperature, then subsequently cooling the sample collection tube 52 to a predetermined temperature, in which case the sample collection tube 52 should be a tube having a standard capacity so that the collected amount can be determined by the standard amount in the tube without requiring the measurement of the flow rate.

Additionally, the selection of the pipe line due to the switching of a six-position selector valve 59 allows the order of the above steps, i.e. the two steps of the sample collection step and the analysis step due to the mass spectrometer, to be switched repeatedly, and therefore enables extremely convenient and efficient use.

EXAMPLE 3

Next, an example 3 of an analysis performed using the above apparatus shown in FIGS. 8 and 9 to analyze the siloxane in a silicon compound gas according to the present invention shall be described.

As a sample collection tube 52, a stainless steel tube having a capacity of 2 cc (inner diameter 5 mm) was filled with stainless steel chips having a grain size of 80 mesh. Then, the six-position selector valve 59 was set in position for the sample collection step as shown in FIG. 8, after which the sample collection tube 52 was heated to 150° C. in preparation for sample collection, and helium gas as an inert gas was fed through the pipe 20 for 30 minutes in a heating procedure in order to expel the water content from inside the sample collection tube 52. Subsequently, the heating of the sample collection tube 52 was stopped, and the cooler 53 was operated to cool the sample collection tube 52 to −110° C. Next, the supply of helium gas was shut off, and monosilane gas as a silicon compound gas S was fed from the storage container 51 to the sample collection tube 52, of which 1000 cc were allowed to flow through (measured by the flow meter F).

Then, the six-position selector valve 59 was operated to switch the position to form the pipe line for the analysis by means of the mass spectrometer 56 as shown in FIG. 9, and the cooling due to the cooler 53 was turned off while operating the heater 54 so as to gradually raise the temperature of the sample collection tube 52 at a rate of approximately 10° C./minute. As a result, helium gas as a carrier gas source He supplied from the carrier gas feed pipe 57 was fed into the sample collection tube 52, and when the gradual rise in the temperature of the sample collection tube 52 caused the temperature to reach the boiling points of specific components, the components having the corresponding boiling points vaporized, in the order of components having lower boiling points, and these components were transported together with the helium gas to the mass spectrometer 56.

Figure 11:
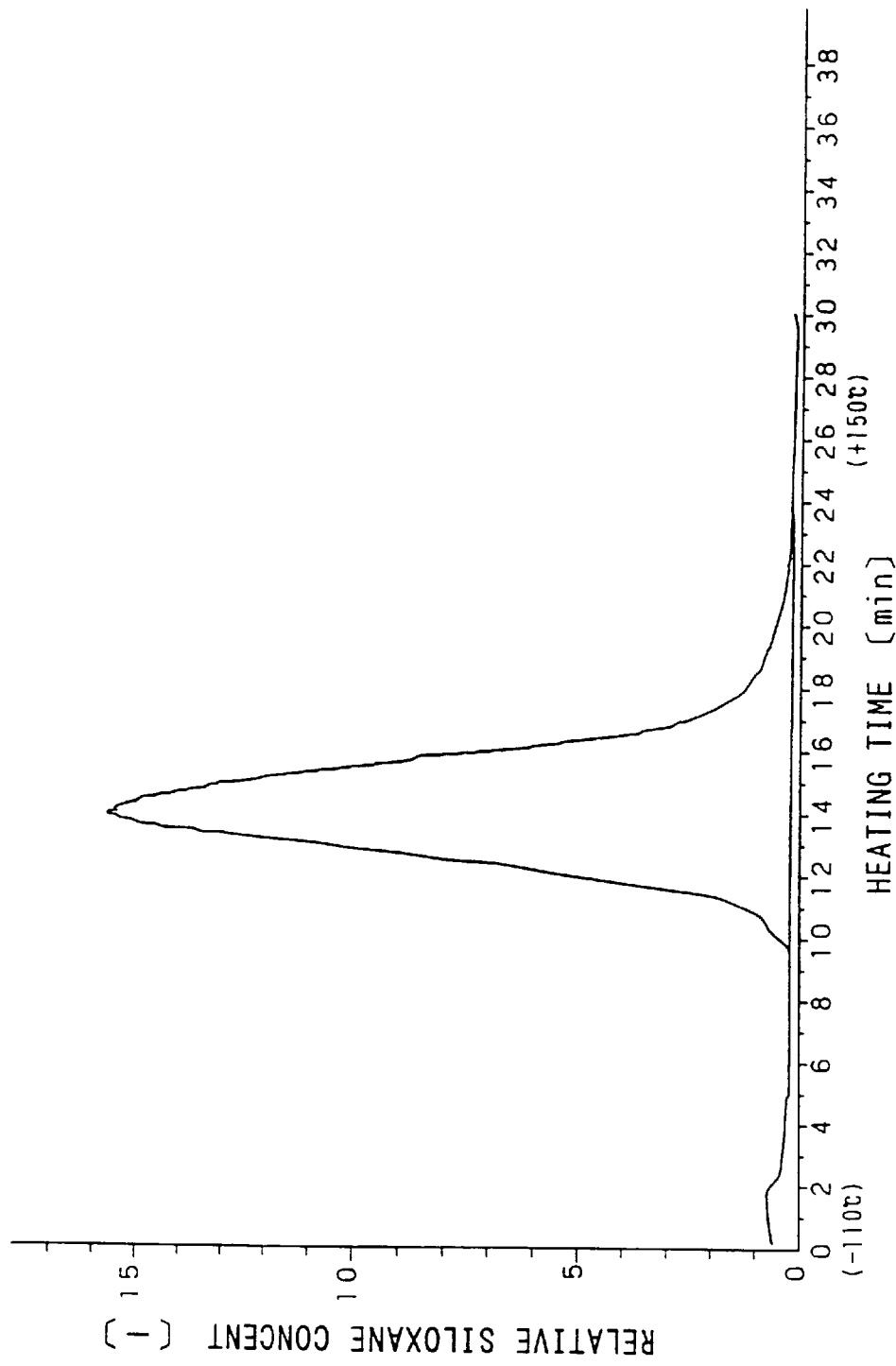
FIG. 11 is a graph showing the results of Example 3 of an analysis method of the present invention.

In the present Example 3, the mass number of the mass spectrometer 56 was fixed at the mas number 77 of siloxane. The results of the measurement of the amount of component having a mass number 77 (siloxane) transported to the mass spectrometer while raising the temperature of the sample collection tube 52 from −110° C. to 150° C. at a rate of approximately 10° C./minute are shown in the graph of FIG. 11 as a relative content of siloxane having a mass number 77 with respect to the temperature raising time (minutes). Upon quantitative analysis of these relative contents with respect to a known reference gas, the content was found to be $4.96 \times 10^{-5}$ cc. Since the amount of the sample was 1000 cc, the concentration was $4.96 \times 10^{-8}$, namely 49.6 ppb.

EXAMPLE 4

Another analysis example shall be explained as Example 4. In this example, the method of analyzing of a standard-capacity sample collection tube held at room temperature was performed with silicon tetrafluoride as the silicon compound gas S, as opposed to Example 3, wherein the sample collection was performed at low temperatures.

That is, in Example 4, a stainless steel standard-capacity sample collection tube 52 of 1000 cc (inner diameter 8 cm, length 19.9 cm) provided with stop valves $V_S$ (not shown in the drawings) on both ends was attached as shown in FIG. 8, and the switch valves $V_S$ were opened. Then, the six-position selector valve 59 was first set in position for the sample collection step shown in FIG. 8, as with Example 3, then the sample collection tube 52 was heated to a temperature of at least 100° C. while feeding inert gas in order to expel the water content from inside the sample collection tube. Subsequently, the sample collection tube 52 was cooled to room temperature, the supply of inert gas was shut off, and silicon tetrafluoride gas at room temperature was fed from the storage container 51 to the sample collection tube 52. After a period of time, the stop valves $V_S$ were closed to collect a sample. Next, the cooler 53 was operated with the stop valves $V_S$ still closed, the sample collection tube 52 was cooled to −110° C., and the six-position selector valve 59 was positioned as shown in FIG. 9 to switch over to the analysis step. At a temperature of −110° C., silicon tetrafluoride solidifies.

Figure 12:
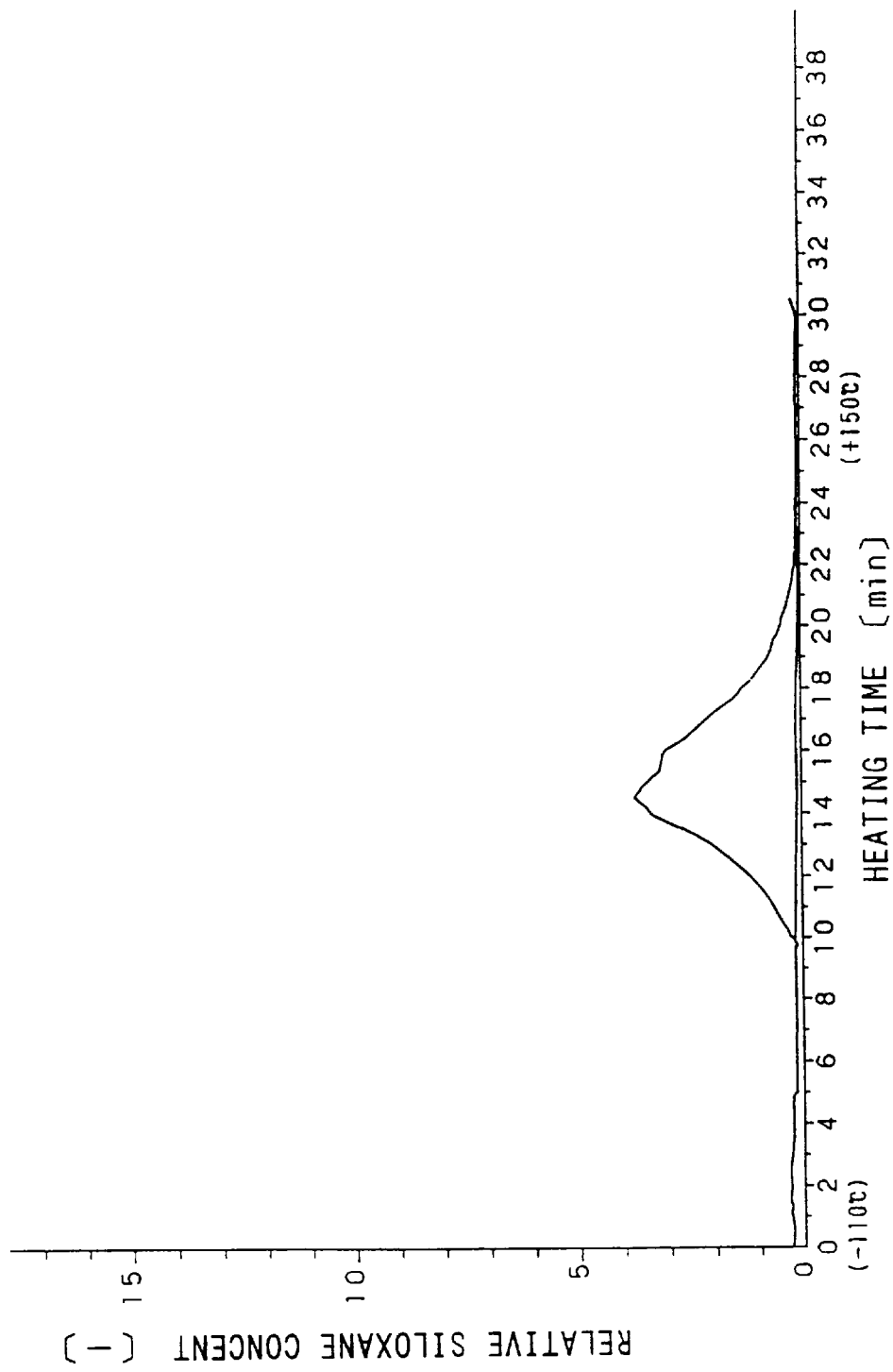
FIG. 12 is a graph showing the results of Example 4 of an analysis method of the present invention.
Figure 13:
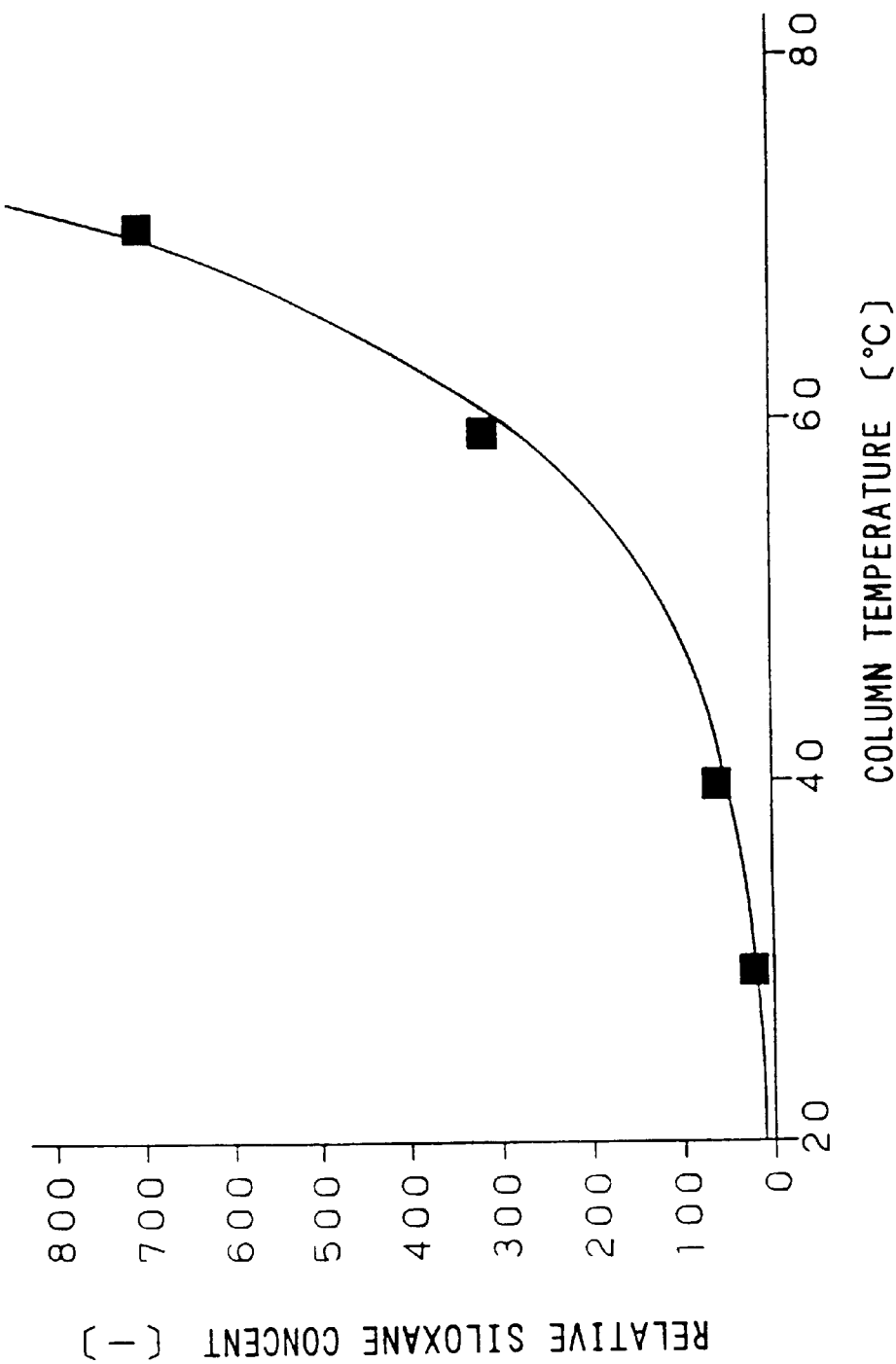
FIG. 13 is a graph showing the changes in the siloxane analysis values accompanying changes in the separator column heating temperature for a conventional analysis method.

Subsequently, the cooling was stopped, and the heater 54 was operated to heat the sample collection tube 52 at a rate of 10° C./minute, and the stop valves $V_S$ provided on the sample collection tube 52 were opened. Then, the helium gas of the carrier gas source He supplied from the carrier gas feed pipe 57 was fed into the sample collection tube 52, so that the gas which was vaporized in the sample collection tube 52 was transported together with the helium gas to the mass spectrometer 56. In this Example 4, the solidified silicon tetrafluoride underwent sublimation at a temperature of −95° C. so as to immediately vaporize without melting, and was transported together with the helium gas through the mass spectrometer 56 to be expelled into the external atmosphere. Then, as the temperature continued to rise, the siloxane which had been condensed began to vaporize at a temperature of −15° C., and was transported together with the helium gas to the mass spectrometer, where the amount of siloxane was measured with the mass number position fixed at a mass number of 77. The results are shown in the graph of FIG. 12. Here, the mass number of the mass spectrometer 56 was fixed at the mass number 77 of siloxane, and the stop valves $V_S$ of the sample collection tube 52 were opened, so as to display the relative amounts of contents having a mass number of 77 detected with respect to the temperature rise time (minutes) when commencing the raise in temperature from −110° C. at a rate of 10° C./minute.

Upon quantitative analysis of the results shown in the graph of FIG. 12 with respect to a reference gas of a known amount, the amount of the content was found to be $1.13 \times 10^{-5}$ cc. Therefore, the concentration of siloxane in the 1000 cc of silicon tetrafluoride was 11.3 ppb.

Additionally, the noise widths of the curves in the graphs of FIGS. 11 and 12 which show the results obtained for Examples 3 and 4 were measured by heightening the sensitivity, and these were converted to sensitivity scales for the above-mentioned graphs, upon which the noise width was found to be 0.36 min. When the lower limit value for detection by the analysis method of the present invention was determined from this value in consideration of the relationship between the concentrations and the curves in the graphs shown in FIGS. 11 and 12 of Examples 3 and 4, the lower limit of detection was found to be 0.3 ppb with a safety factor S/N=2.

While monosilane and silicon tetrafluoride were given as examples of silicon compound gases S in which the siloxane content was measured in Examples 3 and 4 as described above, the present invention is not restricted thereby, and can of course be applied to the analysis of the siloxane content in any of the silicon compound gases shown in Table 1 in which there is the possibility of siloxane being generated and intermixed.

We claim:

1. An apparatus for analyzing a silicon compound gas for siloxane content comprising:
    a valve cage having six pipe mouths arranged along a circumference thereof in the order of a pipe mouth communicating with a silicon compound gas source, a pipe mouth communicating with one side of a sample collection tube provided with cooling means for cooling to a temperature of less than −15° C. and heating means for raising the temperature at a gradual rate, a pipe mouth communicating with a mass spectrometer, a pipe mouth communicating with a carrier gas, a pipe mouth communicating with the other side of the sample collection tube, and a pipe mouth connected to one end of a gas discharge pipe, the other end of which is open to the external atmosphere; and a selector valve element fitted inside said valve cage in airtight fashion such as to be capable of rotating in order to switch between different routes, said selector valve element having six communicating ports positioned such as to be capable of coming into conjunction with the six pipe mouths provided in said valve cage by rotational switching, adjacent pairs of the communicating ports being connected so as to form three pairs of pipe lines;

wherein rotation of the said selector valve element in said valve cage enables switching between a sample collecting state for feeding silicon compound gas into a sample collection tube and collecting siloxane by condensation, and an analysis state for vaporizing the collected siloxane and drawing them into a mass spectrometer for analysis.

2. An apparatus for analyzing a silicon compound gas for siloxane content in accordance with claim 1, wherein the sample collection tube comprises a stainless steel tube filled with at least one filler selected from the group consisting of stainless steel filler and glass filler.

* * * * *